US005538729A

United States Patent [19]
Czinn et al.

[11] Patent Number: 5,538,729
[45] Date of Patent: Jul. 23, 1996

[54] ORAL TREATMENT OF HELICOBACTER INFECTION

[75] Inventors: Steven J. Czinn; John G. Nedrud, both of Cleveland, Ohio

[73] Assignee: OraVax, Inc., Cambridge, Mass.

[21] Appl. No.: 293,565

[22] Filed: Aug. 22, 1994

Related U.S. Application Data

[63] Continuation of Ser. No. 72,162, Jun. 3, 1993, abandoned, which is a continuation of Ser. No. 868,286, Apr. 13, 1992, abandoned.

[51] Int. Cl.$^6$ ............................ A61K 39/02; A61K 39/00; A61K 39/38
[52] U.S. Cl. .................................... 424/234.1; 424/184.1; 424/203.1
[58] Field of Search .............................. 424/234.1, 184.1, 424/203.1

[56] References Cited

U.S. PATENT DOCUMENTS

| 5,268,276 | 12/1993 | Holmgren et al. | 435/69.1 |
| 5,417,986 | 5/1995 | Reid et al. | 424/499 |

FOREIGN PATENT DOCUMENTS

| 9130049.1 | 5/1902 | European Pat. Off. . |
| 2669929 | 6/1992 | France . |
| WO90/04030 | 4/1990 | WIPO . |
| W092/19970 | 11/1992 | WIPO . |
| WO93/07273 | 4/1993 | WIPO . |
| WO93/18150 | 9/1993 | WIPO . |
| W093/16723 | 9/1993 | WIPO . |
| W093/20843 | 10/1993 | WIPO . |

OTHER PUBLICATIONS

Newell, D. G.; Journal of General Microbiology (1987), 133 p. 163–170.

Burr et al, Infection & Immunity 56: 99–105, 1988 Mucosal and Systemic Immunity to *Campylobacter jejuni* in Rabbits after Gastric Inoculation.

McSweegan et al, Infection and Immunity 55: 1431–1435, 1984, Intestinal Mucus Gel and Secretory Antibody Are Barriers to *Campylobacter jejuni* Adherence to INT 407 Cells.

Rappuoli et al, European J. Gastroenterol. Hepatol 5/Suppl 2: S76–S78, 1993, The Development of a Vaccine Against *Helicobacter pylori: A Short Overview.* (Abstract).

Elson et al, The Journ. of Immunology, 132: 2736–2741, 1984, Generalized Systemic & Mucosal Immunity in Mice After Mucosal Stimulation with Cholera Toxin.

Von Wulffen FEMS Microb. Letters 42: 129–133, 1987.

Lycke et al, Immunology 59: 301–308 1986, Strong Adjuvant Properties of Cholera Toxin on Gut Mucosal Immune Responses to Orally Presented Antigens.

Fox et al, Infection and Immunity 59: 785–791, 1991, *Helicobacter felis*: Gastritis in Gnotobiotic Rats: An Animal Model of *H. pylori* Gastritis.

Heap et al, Microb. Ecol. Health Dis 4: S119, 1991 Immunisation & Gastric Colonisation with *Helicobacter felis* (Abstract Only) Oct.

Pavlovskis et al Microb Ecol. Health Dis 4: S10, 1991 Oct. Adjuvant Effect of *E. coli* Heat–labile Enterotoxin on Host Immune Response Following Vaccination with Non–labile Campylobacter Antigens.

Baskerville and Newell, Naturally Occurring Chronic Gastritis and *C pylori* Infection in the Rhesus Monkey: A Potential Model for Gastritis in Man, Gut 29:465–472, 1988.

Parsonnet et al., VIth Int. Workshop of *Campylobacter, Helicobacter*, and Related Organisms. Oct. 7–10, 1991.

Blaser, Gastric *Campylobacter*–like Organisms, Gastritis, and Peptic Ulcer Disease, Gastroenterolgy 93:371–83, 1987.

Bowie et al., Deciphering the Message in Protein Sequences: Tolerance to Amino Acid Substitutions, Science 247:1306–1310, 1990.

Burr et al., Mucosal and Systemic Immunity to *Campylobacter jejuni* in Rabbits after Gastric Inoculation, Infection and Immunity 56:99–105, 1988.

Chamberlain et al., *Campylobacter (Helicobacter) pylori* Is Peptic Disease a Bacterial Infection? Arch. Intern Med. 150:951–955, 1990.

Chen et al., Lack of Protection Against Gastric Helicobacter Infection Following Immunisation with Jack Bean Urease: The rejection of a Novel Hypothesis, FEMS Microbiology Letters 116:245–250, 1994.

Chen et al., Immunisation Against Gastric Helicobacter Infection in a Mouse/*Helicobacter felis* Model, The Lancet 339:1120–1121, 1992.

Clayton et al., Molecular Cloning and Expression of *Campylobacter pylori* Species–Specific Antigens in *Escherichia coli* K–12, Infection and Immunity 57:623–629, 1989.

Clayton et al., Nucleotide Sequence of Two Genes from *Helicobacter pylori* Encoding for Urease Subunits, Nucleic Acids Research 18:362, 1990.

Clements et al., Adjuvant Activity of *Escherichia coli* Heat––labile Enterotoxin and Effect on the Induction of Oral Tolerance in Mice to Unrelated Protein Antigens, Vaccine 6:269–277, 1988.

Coelho et al., Duodenal Ulcer and Eradication of *Helicobacter pylori* in a Developing Country, Scandinavian J. Gastroenterolgy 27:362–366, 1992.

Crabtree et al., Mucosal Humoral Immune Response to *Helicobacter pylori* in Patients with Duodenitis, Digestive Diseases and Sciences 36:1266–1273, 1991.

Czinn and Nedrud, Oral Immunization Against *Helicobacter pylori*, Infection and Immunity 59:2359–2363, 1991.

(List continued on next page.)

*Primary Examiner*—James C. Housel
*Assistant Examiner*—Ginny Allen Portner
*Attorney, Agent, or Firm*—Fish & Richardson

[57] ABSTRACT

Method of eliciting in a mammalian host a protective immune response to Helicobacter infection, by orally administering to the host an immunogenically effective amount of Helicobacter antigen. Vaccine compositions are also provided.

5 Claims, 1 Drawing Sheet

OTHER PUBLICATIONS

Czinn and Carr, Rapid Diagnosis of *Campylobacter Pyloridis*–associated Gastritis, J. Pediatrics 110:569–570, 1987.

Czinn et al., Protection of Germ–free Mice from Infection by *Helicobacter felis* after Active Oral or Passive IgA Immunization, Vaccine 11:637–642, 1993.

Davin et al., Proceedings of the DDW, American Gastroenterological Association, May 16–19, 1993, 1213, A–304.

Dick–Hegedus and Lee, Use of a Mouse Model to Examine Anti– *Helicobacter pylori* Agents, Scandinavian Journal of Gastroenterology, 26:909–915, 1991.

Donaldson and Toskes, The Relation of Enteric Bacterial Populations to Gastrointestinal Function and Disease, Gastrointestinal Disease, 3rd Edition, (W. B. Saunders Co., Philadelphia 1983) pp. 44–54.

Drazek et al., Characterization and Presumptive Identification of *Helicobacter pylori* Isolates from Rhesus Monkeys, J. Clin. Microbiology 32:1799–1804, 1994.

Dubois et al., Natural Gastric Infection with *Helicobacter pylori* in Monkeys: A Model for Spiral Bacteria Infection in Humans, Gastroenterology 106:1405–1417, 1994.

Dunn et al., Purification and Characterization of Urease from *Helicobacter pylori*, J. Biol. Chem. 265:9464–9469, 1990.

Eaton et al., Essential Role of Urease in the Pathogenesis of Gastritis Induced by *Helicobacter pylori* in Gnotobiotic Piglets, Gastroenterology 98:A654, 1990.

Eaton et al., *Campylobacter pylori* Virulence Factors in Gnotobiotic Piglets, Infection and Immunity 57:1119–1125, 1989.

Eldridge et al., Biodegradable Microspheres: Vaccine Delivery System for Oral Immunization, Current Topics in Microbiology and Immunology 146:59–66, 1989.

Elson and Ealding, Generalized Systemic and Mucosal Immunity in Mice After Mucosal Stimulation with Cholera Toxin, J. Immunology 132:2736–2741, 1984.

Elson et al., A Levage Technique Allowing Repeated Measurement of IgA Antibody in Mouse Intestinal Secretions, J. Immunological Methods 67:101–108, 1984.

Engstrand et al., Inoculation of Barrier–Born Pigs with *Helicobacter pylori*: a Useful Animal Model for Gastritis Type B, Infection and Immunity 58:1763–1768, 1990.

Evans et al., Characterization of the *Helicobacter pylori* Urease and Purification of its Subunits, Microbial. Pathogenesis 10:15–26, 1991.

Ferrero and Labigne, Cloning, Expression and Sequencing of *Helicobacter felis* Urease Genes, Molecular Microbiology 9:323–333, 1993.

Fox et al., *Helicobacter felis* Gastritis in Gnotobiotic Rats: an Animal Model of *Helicobacter pylori* Gastritis, Infection and Immunity 59:785–791, 1991.

Fox et al., *Campylobacter mustelae*, a New Species Resulting from the Elevation of *Campylobacter pylori* subsp. *mustelae* to Species Status, International J. Systemic Bacteriology 39:301–303, 1989.

Fox et al., Gastric Colonization by *Campylobacter pylori* subsp. *mustelae* in Ferrets, Infection and Immunity 56:2994–2996, 1988.

Fox et al., *Helicobacter mustelae*–Associated Gastritis in Ferrets, Gastroenterology 99:352–361, 1990.

Fubara and Freter, Protection Against Enteric Bacterial Infection by Secretory IgA Antibodies, J. Immunology 111:395–403, 1973.

Gilligan and Po et al., Oral Vaccines: Design and Delivery, International Journal of Pharmaceutics 75:1–24, 1991.

Goodwin et al., Transfer of *Campylobacter pylori* and *Campylobacter mustelae* to *Helicobacter* gen. nov. as . . . *Helicobacter mustelae* comb. nov., Respectively, International J. Systematic Bacteriology 39:397–405, 1989.

Gootz et al., Immunological and Molecular Characterization of *Helicobacter felis* Urease, Infection and Immunity, 62, 793–798, 1994.

Graham, *Campylobacter pylori* and Peptic Ulcer Disease, Gastroenterology 96:615–25, 1989.

Gupta et al., Adjuvants—a Balance Between Toxicity and Adjuvanticity, Vaccine 11:293–306, 1993.

Guruge et al., Detection of Antibodies to *Helicobacter pylori* Cell Surface Antigens, Scand. J. Infect. Dis. 22:457–465, 1990.

Handt et al., *Helicobacter pylori* Isolated from the Domestic Cat: Public Health Implications, Infection and Immunity 62:2367–2374, 1994.

Heap and Lee, Immunisation and Gastric Colonisation with *Helicobacter felis*, Microb. Ecol. Health Dis. 4:s119; VIth International Workshop on Campylobacter, Helicobacter and Related Organisms, Oct. 7–10, 1991.

Holmgren et al., New Cholera Vaccines, Vaccine 7:94–96, 1989.

Hu and Mobley, Purification and N–Terminal Analysis of Urease from *Helicobacter pylori*, Infection and Immunity 58:992–998, 1990.

Hu et al., Purification of Recombinant *Helicobacter pylori* Urease Apoenzyme Encoded by *ureA* and *ureB*, Infection and Immunity 60:2657–2666, 1992.

Kazi et al., Cellular and Humoral Immune Responses in *Campylobacter pylori*–associated Chronic Gastritis, J. Pathology 159:231–237, 1989.

Keusch and Bart, Immunization Principles and Vaccine Use, Harrison's Principles of Internal Medicine, 13th Edition vol. 1, pp. 498–511.

Labigne et al., Shuttle Cloning and Nucleotide Sequences of *Helicobacter pylori* Genes Responsible for Urease Activity, J. Bacteriology 173:1920–1931, 1991.

Lee et al., Pathogenicity of *Helicobacter pylori*: A Perspective, Infection and Immunity 61:1601–1610, 1993.

Lee et al., A Small Animal Model of Human *Helicobacter pylori* Active Chronic Gastritis, Gastroenterology 99:1315–1323, 1990.

Lee et al., Protection from Helicobacter Infections by Intragastric Immunization with Recombinant Urease, *Helicobacter pylori*: Basic Mechanisms to Clinical Cure, Poster Abstracts, Nov. 3–6, 1993 (Poster #13).

Lycke and Holmgren, Strong Adjuvant Properties of Cholera Toxin on Gut Mucosal Immune Responses to Orally Presented Antigens, Gastroenterology 59:301–308, 1986.

Mazanec et al., Immunoglobulin A Monoclonal Antibodies Protect Against Sendai Virus, J. Virology 61:2624–2626, 1987.

McGhee et al., The Mucosal Immune System: From Fundamental Concepts to Vaccine Development, Vaccine 10:75–88, 1992.

McSweegan et al., Intestinal Mucus Gel and Secretory Antibody are Barriers to *Campylobacter jejuni* Adherence to INT 407 Cells, Infection and Immunity 55:1431–1435, 1987.

Merrifield, Solid Phase Peptide Synthesis. I. The Synthesis of Tetrapeptide, 85:2149–2154, 1963.

Mestecky, The Common Mucosal Immune System and Current Strategies for Induction of Immune Responses in External Secretions, J. Clin. Immunology 7:265–276, 1987.

Mobley et al., *Helicobacter pylori* Urease: Properties and Role In Pathogenesis, Proceeding of an International Workshop at Deerhurst, Huntsville, Ontario, Canada. 21–24, Feb. 1991. pp. 39–46.

Morris and Nicholson, Ingestion of *Campylobacter pyloridis* Causes Gastritis and Raised Fasting Gastric pH, Am. J. Gastroenterology 82:192–199, 1987.

Nagata et al., Monoclonal Antibodies Against the Native Urease of *Helicobacter pylori*: Synergistic Inhibition of Urease Activity by Monoclonal Antibody Combinations, Infection and Immunity 60:4826–4831, 1992.

Nedrud et al., Combined Oral/Nasal Immunization Protects Mice from Sendai Virus Infection, J. Immunology 139:3484–3492, 1987.

Oderda et al., Eighteen Month Follow Up of *Helicobacter pylori* Positive Children Treated with Amoxycillin and Tinidazole, Gut 33:1328–1330, 1992.

Offit and Clark, Protection Against Rotavirus–Induced Gastroenteritis in a Murine Model by Passively Acquired Gastrointestinal But Not Circulating Antibodies, J. Virology 54:58–64, 1985.

O'Hagan, Intestinal Translocation of Particulates—Implications for Drug and Antigen Delivery, Advanced Drug Delivery Reviews 5:265–285, 1990.

Olivieri et al., Growth of *Helicobacter pylori* in Media Containing Cyclodextrins, J. Clinical Microbiology 31:160–162, 1993.

Orenstein et al., Immunization, Mandell, Douglas and Bennett's Principles and Practice of Infectious Diseases, 4th Ed. (Churchill Livingstone, New York) Part IV, pp. 2770–2790.

Pallen et al., Vaccine against *Helicobacter pylori* Urease, The Lancet 336:186–187, 1990.

Parsonnet et al., *Helicobacter pylori* Infection in Intestinal- and Diffuse–Type Gastric Adenocarcinomas, J. National Cancer Institute 83:640–642, 1991.

Pavlovskis et al., Adjuvant Effect of *Escherichia coli* Heat--labile Enterotoxin on Host Immune Response ... Campylobacter Antigens, Microb. Ecol. Health Dis. VIth Int. Workshop on Campylobacter ... Oct. 7–10, 1991.

Peterson, *Helicobacter pylori* and Peptic Ulcer Disease, New England Journal of Medicine 324:1043–1048, 1991.

Rappuoli et al., Development of a Vaccine Against *Helicobacter pylori*: A Short Overview, Eur. J. Gastroenterol. Hepatol. 5/Suppl. 2, 1993.

Rauws et al., *Campylobacter pyloridis*–Associated Chronic Active Antral Gastritis, Gastroenterology 94:33–40, 1988.

Schaedler and Orcutt, Gastrointestinal Microflora, Chapter 14, The Mouse in Biomedical Research, vol. III (Academic Press, Inc. 1983) pp. 341–345.

Stacey et al., Local and Systemic Antibody Responses During *Helicobacter pylori* Infections, *Helicobacter pylori* and Gastroduodenal Pathology, Pajares et al. (Eds.) (Springer–Verlag, New York, 1993) pp. 165–169.

Stuart et al., Further Studies on Urease Production by Proteus and Related Organisms, J. Bacteriol. 49:437–444, 1945.

Thomas et al., Effect of Oral Immunization with *Helicobacter pylori* Antigens on Colonization by *H. felis* in Mice, Acta Gastro–Enterologica Belgica, VII Int. Workshop on Campylobacter ... Brussels, Sep. 21–25, 1993.

Von Wulffen, Low Degree of Relatedness Between *Campylobacter pyloridis* and Enteropathogenic *Cmpylobacter* ... by DNA–DNA Blot Hybridization and Immunoblot Studies, FEMS Microbiology Letters 42:129–133, 1987.

Wegmann et al., Gastrospirillum–hominis–assoziierte Gastritis—Eine Zoonose?, Schwetz med. Wschr. 121:245–254, 1991.

Winner III et al., New Model for Analysis of Mucosal Immunity: Intestinal Secretion of Specific Monoclonal ... Hybridoma Tumors Protects Against *Vibrio cholerae* Infection, Infection and Immunity 59:977–982, 1991.

Wotherspoon et al., Regression of Primary Low–grade B–cell Gastric Lymphoma of Mucosa–associated Lymphoid Tissue Type After Eradication of *Helicobacter pylori*, The Lancet 342:575–577, 1993.

Wyatt et al., Local Immune Response to Gastric *Campylobacter* in Non–ulcer Dyspepsia, J. Clin. Pathol. 39:863–870, 1986.

Abstracts Submitted for *Helicobacter Pylori*: Beginning the Second Decade and the VIIth Workshop of the European *Helicobacter pylori* Study Group, Houston, Texas, Sep. 30–Oct. 1, 1994.

Hawtin et al., Investigation of the Structure and Localization of the Urease of *Helicobacter pylori* Using Monoclonal Antibodies, J. General Microbiology 136:1995–2000, 1990.

Czinn et al., Serum and Mucosal Immune Response Following Oral Immunization with *Helicobacter pylori*, Gastroenterology 100:A571, 1991.

Czinn et al., Oral Immunization Protects Germ–Free Mice Against Infection from *Helicobacter felis*, Gastroenterology 102:A611, 1992.

Czinn et al., Oral Immunization Against *Helicobacter pylori*, Infection and Immunity 59:2359–2363, 1991.

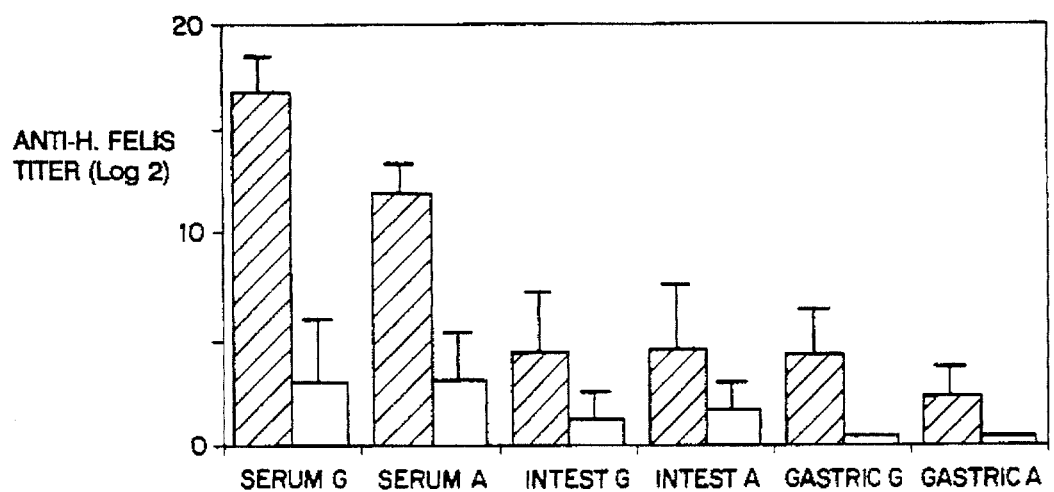
FIG. 1
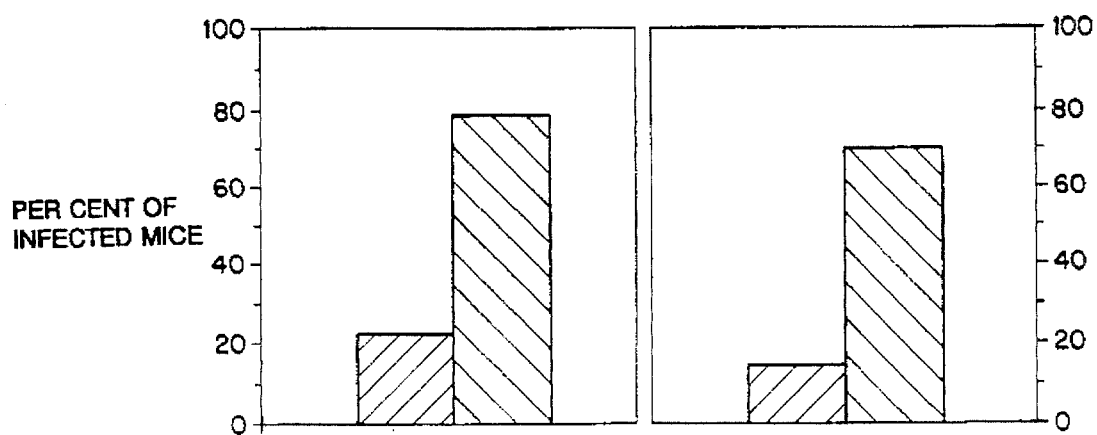
FIG. 2A  FIG. 2B

ORAL TREATMENT OF HELICOBACTER INFECTION

This is a continuation of application Ser. No. 08/072,162, filed Jun. 3, 1993, now abandoned, which is a continuation of application Ser. No. 07/868,286, filed Apr. 13, 1992, abandoned.

The present invention relates to the treatment of gastric infection in mammals, including humans. More particularly, the present invention relates to a method for the treatment of Helicobacter infection in mammals, including humans, and to vaccine compositions and antibodies suitable for use in such treatment.

BACKGROUND OF THE INVENTION

*Helicobacter pylori* (*H. pylori*) infection of human gastric epithelium is a major factor in the development of gastritis and ulcers and may be a risk factor for the development of gastric cancer[1-3]. This slender S-shaped gram negative microorganism is routinely recovered from gastric tissue of adults and children with histologic evidence of gastritis or peptic ulceration. Evidence for a causal relationship between *H. pylori* and gastroduodenal disease comes from studies in human volunteers, gnotobiotic pigs, and germ-free rodents whereby postulates by Koch were satisfied by creating histologically confirmed gastritis following consumption of viable microorganisms[4-11]. Although difficult to treat, when eradication is achieved the underlying gastritis resolves and, in patients with duodenal ulcer disease, the recurrence rate of the ulcer decreases dramatically[12].

In spite of in vitro susceptibility to many antimicrobial agents, in vivo long-term eradication of established *H. pylori* infections with antimicrobial agents is difficult to achieve[18]. The microorganism is found within the mucous coat overlying the gastric epithelium. This is a location which does not appear to allow for adequate antimicrobial levels to be achieved when given orally. At the present time, most authorities recommend a "triple therapy", namely a bismuth salt in combination with tetracycline and metronidazole for 2–4 weeks. However, the effectiveness of this or other chemotherapeutic regimens remains suboptimal.

At the present time little is known regarding the role of the mucosal immune system in the stomach. The distribution of Ig producing cells in the normal gastric antrum indicates that IgA plasma cells make up 80% of the total plasma cell population. In addition, the number of plasma IgA cells present in the gastric antrum is comparable to other mucous membranes[25,26]. Although a number of studies have looked at immunoglobulin levels in various endocrine fluids, no data is available regarding the concentration of immunoglobulins in gastric secretions. Moreover there is only limited data to suggest that patients infected with *H. pylori* develop specific IgG and/or IgA antibodies in gastric aspiarates[32]. Thus once infection is established, neither antibody nor antibiotics are very effective at eradication.

Czinn et al have shown that repetitive oral immunizations with *H. pylori* antigens and cholera toxin result in the inducement of a vigorous gastrointestinal IgA anti-*H. pylori* response in mice and ferrets[18] However, since mice and ferrets are resistant to *H. pylori* infection and since no small animal model existed at that time to evaluate protection, it was unknown whether the antibodies so formed were protective.

Lee et al have reported the ability to infect germ-free rodents with *H. felis* and reproducibly document histologic gastritis[9, 10] However no evaluation of protection has been reported.

There remains a need therefore for an effective treatment of *H. pylori* gastric infection, especially in humans. The present invention seeks to fill that need.

SUMMARY OF THE INVENTION

The present inventors have discovered, surprisingly, that oral immunization of a host with Helicobacter antigen results in the formation of antibodies which are protective against acute infection by Helicobacter microorganisms. The formation of such protective anibodies was not predictable on the basis of prior work since, prior to the present invention, no suitable model existed to evaluate protection.

According to one aspect of the present invention, there is provided a method of eliciting in a mammalian host a protective immune response to Helicobacter infection, comprising orally administering to the host an immunogenically effective amount of Helicobacter antigen to elicit the desired protective immune response.

According to another aspect of the present invention, there is provided a vaccine composition comprising an amount of Helicobacter antigen effective to elicit a protective human response in a patient, in association with a pharmaceutically acceptable diluent.

According to a further aspect of the present invention, there is provided a method of imparting to a mammalian host passive protection to Helicobacter infection, comprising orally administering to the host a immunologically effective amount of a Helicobacter specific IgA antibody to impart the desired passive protection.

According to yet another aspect of the present invention, there is provided a murine *H. felis* specific IgA or IgG monoclonal antibody.

According to a yet further aspect of the invention, there is provided a cell line #71-$G_5$-$A_8$.

BRIEF DESCRIPTION OF THE DRAWINGS

The invention will now be further described with reference to the accompanying figures, in which:

FIG. 1 is is a bar chart of antibody titers in various sera and secretions of germ free mice after oral immunization with *H. felis* lysate in association with cholera toxin; and FIGS. 2A and 2B are bar charts of percent of mice infected with *H. felis* after active immunization (FIG. 2A) and passive immunization (2B) compared with controls.

DETAILED DESCRIPTION OF THE INVENTION

The present inventors have demonstated that oral immunization in mice using *H. felis* antigen produces a protective immune response wherein antigen specific protective antibodies are present in gastric secretions. The effect of the protective immune response is that immunized animals when challenged with pathogen do not become infected in comparison to non-immunized animals which do become infected. While not being bound by any theory, the present inventors believe that oral immunization with the *H. felis* antigen stimulates the common mucosal immune system and perhaps local sites in the gastric mucosa resulting in the appearance of *H. felis* specific IgA antibodies in the gastric secretions, which prevent *H. felis* infection. Since *H. felis* and *H. pylori* are similar species from the same genus (Helicobacter), it is reasonable to conclude that immunization of for example a germ-free pig with H. pylori antigen plus a mucosal adjuvant such as cholera toxin will be effective in preventing H. pylori infection of the stomach. Since it is a routine matter to conduct pre-clinical trials of candidate vaccines for human use in animal models, it is believed that the methodology of the present invention is effective in humans, especially in the treatment of H. pylori infection in humans.

It has been discovered by the present inventors that an H. felis germ-free mouse model can be employed to evaluate antibody protection levels following immunization with H. felis antigen. FIG. 1 relates to the results obtained in experiments with the H. felis germ-free mouse model. Oral immunization of the model with bacterial antigens in association with cholera toxin resulted in elevated serum, gastric and intestinal anti-H. felis antibody titers and protection from acute infection of the stomach by H. felis pathogen. In the experiments, groups of Swiss-Webster germ-free mice (Taconic) were orally immunized 4 or 5 times over a one month period with 2–4 mg of sonicated H. felis lysate plus 10 µg of cholera toxin. The mice were then challenged orally with approximately $10^6$ viable H. felis bacteria. The mice were sacrificed and intestinal and gastric secretions collected as described in the following working Examples. Anti-H. felis antibody titers were determined by ELISA. The black solid bars in FIG. 1 represent mean titers (±S. D.) from immunized mice and the open bars represent mean titers (±S. D.) from the control non-immunized mice. The results presented graphically in FIG. 1 are summarized in Table 1 below.

TABLE 1

| ANTIBODY TITER ($LOG_2$) | | | | | | |
|---|---|---|---|---|---|---|
| | Serum | | Gastric | | Intestine | |
| | IgA | IgG | IgA | IgG | IgA | IgG |
| CONTROL | 3.1 | 3 | 0 | 0 | 1.6 | 1.1 |
| IMMUNIZED | 11.8 | 16.8 | 2.1 | 4.25 | 4.5 | 4.4 |

| H. FELIS INFECTION | | |
|---|---|---|
| | H. felis (+) | H. felis (−) | PROTECTION |
| Control n = 18 | 14 | 4 | 23% |
| Immunized n = 17 | 4 | 13 | 78% |

It can be seen from the above results that significantly higher antibody titers are observed for the immunized mice than for the control animals.

FIGS. 2A and 2B depict the results of studies to establish the protection against infection by H. felis by conducting active and passive immunization experiments. Referring to the active immunization experiments, gastric biopsies were collected at sacrifice from the H. felis challenged mice in the experiments described above in connection with FIG. 1. The biopsies were scored for the presence of H. felis by rapid urease test and/or culture positivity, described in the following working Examples. FIG. 2A shows the results of pooled data from 3 experiments (n=17 immunized animals and 18 control animals). The black (solid) bars represent challenged immunized mice and the striped bars the control non-immunized mice.

It will be seen that from a total of 17 immunized animals, only 4 became infected, as compared to 14 of the 18 control animals. In other words 78% percent of the immunized animals were protected from H. felis infection as compared to 23% of the non-immunized animals The fact that protection was the direct result of IgA antibodies was established by passive immunization of germ-free mice with H. felis specific IgA monoclonal antibodies and comparison of the resulting protection with that exhibited by mice given no antibody or irrelevant antibody (for example Sendai virus specific IgA monoclonal antibody). The results are set forth in FIG. 2B.

An IgA monoclonal antibody reactive with H. felis was isolated and subcloned after an immunization protocol similar to that described in FIG. 1. Ascites containing H. felis specific IgA monoclonal antibody produced from the cell line #71-$G_5$–$A_8$, prepared as described in the working Examples, or Sendai virus specific IgA monoclonal antibody or saline were orally administered to germ-free mice at the time of infection with H. felis, and 4, 8, and 24 hours later. Seven days after infection, the mice were sacrificed and gastric biopsies scored for H. felis (n=7 mice received H. felis specific monoclonal antibody and 13 mice received no antibody or Sendai virus specific monoclonal antibody). The black sold bars represent the mice which received the H. felis specific monoclonal antibody and the striped bars represent the mice which received either Sendai virus specific monoclonal antibody or saline (no antibody).

These results establish that IgA alone protects against H. felis infection of the gastric mucosa.

It is also observed that oral administration of H. felis antigen results in significantly increased levels of anti-H. felis IgG antibodies as well as IgA antibodies. There are a number of possible explanations for this phenomenon. First, it has been observed that cholera toxin can, in some cases, enhance both antigen-specific IgA and IgG responses[22]. Secondly, cell traffic studies have shown that mesenteric node IgG lymphocytes are a component of the mucosal immune system and can give rise to mucosal IgG plasma cells which have been observed in gastric mucosa. Thirdly, at least a portion of the observed gastric IgG could be the result of transudation of serum antibody into the gastric lumen secondary to mild to moderate inflammation observed in both control and immunized animals.

The above discussion has focussed on the use of H. felis antigen in the treatment of H. felis infection. It will be appreciated however that the present invention is not limited to the treatment of H. felis infection.

Thus, the present invention also includes within its scope the treatment or prophylaxis of mammals, including humans, for H. pylori infection, wherein the patient is orally immunized with an immunologically effective amount of H. pylori antigen in order to elicit the formation of protective antibodies to H. pylori pathogen. Preferably, the H. pylori is administered in association with a mucosal adjuvant, for example cholera toxin.

Moreover, the present invention includes within its scope the passive immunization of mammals, including humans, against H. pylori infection. This is achieved by orally administering an effective amount of an H. pylori specific antibody to the patient. Preferably an H. pylori specific IgA monoclonal antibody is orally administered to the patient.

The vaccine of the invention is administered orally in amounts readily determined by persons of ordinary skill in this art. Thus, for adults, a suitable dosage would be in the range of 10 µg to 10 mg, for example 50 µ g to 5 mg. Similar dosage ranges would be applicable for children.

As noted above, a suitable mucosal adjuvant is cholera toxin. Others which may be used are non-toxic derivatives of cholera toxin, including its B subunit and/or conjugates of antigen plus cholera toxin or its B subunit, microcapsules, or immune stimulating complexes (ISCOM's) or liposomes and attenuated live vectors such as viruses or Salmonella bacteria. The amount of mucosal adjuvant employed depends on the type of mucosal adjuvant used. For example, when the mucosal adjuvant is cholera toxin, it is suitably used in an amount of 5 µg to 50 µg, for example 10 µg to 35 µg. When used in the form of microcapsules, the amount used will depend on the amount employed in the matrix of the microcapsule to achieve the desired dosage. This is something within the skill of a person of ordinary skill in this art.

Suitable carriers and diluents are enteric coated capsules and/or 0.2N NaHCO$_3$ and/or saline.

EXAMPLES

The invention will now be further described by the following non-limiting examples.

(a) The Mice

The mice used in the experiments were germ-free Swiss Webster mice (8 weeks old) were obtained from Taconic (Germantown, N.Y.). The animals were housed in microisolater cages under germ-free conditions and they were allowed free access to autoclaved laboratory chows and water. With the exception of occasionally isolating diphtheroids, animals were maintained in a germ-free state throughout the immunization protocol.

(b) Bacterial Strains

Bacteria recovered from gastric biopsy specimens of a cat were identified as *H. felis* based on morphology, Gram stain, and the production of urease, catalase and oxidase[9]. Organisms were stored in 50% phosphate-buffered saline (PBS). 25% glycerol: heated fetal calf serum at $-70°$ C. Bacteria used in the the following examples were passaged in vitro two to three times after isolation.

(c) Bacterial Antigens

The test strain was inoculated onto Columbia agar (Difco, Detroit, Mich.) containing 7% horse blood and incubated microaerophilically at $37°$ C. for 5–7 days. The organisms were harvested in PBS and the resulting suspensions were sonicated to lyse the bacteria at $40°$ C., cleared of cellular debris by low-speed centrifugation, and sterile filtered. These whole-cell sonicates were stored as 100 µl aliquots at $-70°$ C. until needed for oral immunization of animals.

(d) Outer membranes

Outer membranes were prepared as described[19]. Briefly, bacterial suspensions were treated with 1 mg of ribonuclease and deoxyribonuclease (Sigma Chemical, St. Louis) in 0.5M Tris-EDTA buffer (pH 7.8) at $4°$ C. immediately prior to sonication and low-speed centrifugation as above. Bacterial envelopes were then separated from the cleared lysate by ultracentrifugation at 150,000× g for 1 h. Outer membranes were separated from the cell envelopes by differential solubilization in sodium n-lauroylsarcosine and recovered by ultracentrifugation. The resulting pellets were suspended in 0.05M phosphate buffer (pH 7.0), divided into aliquots, and stored at $-70°$ C. Protein concentration was determined by the method of Lowry et al for use in ELISA[20].

Example 1

Mice were lightly anesthesized by i.p. injection of 1.0 mg ketamine prior to intragastric immunization. Then, whole cell sonicate preparations plus 10 µg of cholera toxin (List Biologicals, Campbell, Calif.) were suspended in 0.2M NaHCO$_3$, and 0.5 ml was delivered to the stomachs of mice by intubation through polyethylene tubing attached to a hypodermic syringe. This procedure will be referred to as oral immunization.

To examine the possibility of developing functional immunity, three oral immunization protocols were evaluated. Protocol 1 consisted of 4 oral immunizations over 1 month consisting of 2 mg *H. felis* lysate plus cholera toxin (a known mucosal adjuvant). Protocol 2 increased the *H. felis* to 4 mg per immunization plus cholera toxin, and protocol 3 consisted of 5 oral immunizations over 6 weeks each containing 4 mg of *H. felis* lysate plus cholera toxin. Unless otherwise noted, animals were challenged 7–10 days after the last immunization and sacrificed 3–7 days later.

The following tissue fluids were collected: serum, gastric secretions, and intestinal secretions. These samples were then titrated for the presence of anti-*H. pylori* antibodies by enzyme-linked immunosorbent assay (ELISA). In addition, gastric biopsies were obtained for rapid urease test and culture. Infection was defined as positive if either culture or rapid urease test (see below) was positive. Serum was obtained by tail vein bleeding and letting the blood clot at room temperature. Gastric and intestinal secretions were collected by a modification of the procedure of Elson et al[21, 22]. Briefly, gastric and intestinal secretions from mice were collected separately. Stomachs and intestines were removed and injected with 2.0 ml of a polyethylene glycol-based lavage plus anti-protease solution. The gastric lavage contained Tris buffer to neutralize gastic acid.

The ELISA was carried out as follows. Murine samples were assayed for *H. felis* antibodies as follows. Ninety-six well polystyrene microtiter plates were coated with 100 µl/well of appropriate outer membrane proteins (20 µg/ml) overnight at $4°$ C. Non-specific binding sites were blocked with BSA in PBS for 90 minutes at room temperature and then the plates were washed with 0.1% BSA in PBS. Samples were tested in duplicate at dilutions ranging from neat to 1:512,000 and 100 µl of each dilution per well was added to the antigen-coated plates. Following incubation at room temperature for 90 minutes, the plates were washed three times with 0.1% BSA in PBS, and 100 µl of a 1:1000 dilution of goat anti-mouse IgA or IgG alkaline phosphatase conjugate (Zymed, San Francisco, Calif.) was added to each well for 90 minutes. After washing, the plates were developed with 100 µl per well of a 1 mg/ml solution of p-nitrophenyl phosphate in glycine buffer (pH 9.6) for 1 hour. The absorbance at 410 nm was measured in each well using a Dynatech MR 700 Microtiter Plate Reader. The antibody titer was defined as the reciprocal of the highest dilution yielding an optical density of 0.05 above wells which contained antigen and which were incubated with the antibody conjugate but without the primary antibody sample The rapid urease test was carried out as follows. Two gastric biopsy specimens of 10 mg wet weight from each mouse were immediately placed in 0.2 mL Stuart urease test broth[28] and incubated at room temperature. The presence of urease was determined by color change from yellow to pink in the test broth after 4 hours[24].

Cultures were obtained as follows. Gastric antral biopsies were homogenized and plated onto Columbia agar containing 5% sheep blood, and incubated at $37°$ C under microaerophilic conditions (gas generating kit; Oxoid Ltd., London, UK). A positive culture was defined as visible growth after 5 days. All isolates were identified as *H. felis* based on morphology, gram stain and the production of urease, catalase and oxidase.

Despite minor changes in experimental design among the three groups, no appreciable differences in immune response were noted. Thus, the data were pooled and the geometric means of gastric lavage, intestinal lavage, and serum antibody titers from the 13 control and 12 immunized animals studied are set forth in Table 1 and FIG. 1 discussed above.

Although these animals were both immunized and challenged, the antibody titers did not differ significantly from mice which were immunized and not challenged. In these experiments, gastric, intestinal and serum IgA and IgG antibody titers were significantly higher than that observed in the unimmunized control animals. Specifically, there was a 4-fold increase in gastric IgA (p=.001), an 8-fold increase in intestinal IgA (p=.0038) and a 350-fold increase in serum IgA (p=.0001) compared with unimmunized control animals. Similarly, a significant elevation of gastric IgG (p=.0009), intestinal IgG (p=.0001), and serum IgG (p=.0001) was observed.

To evaluate protection from *H. felis* infection, gastric biopsies were taken from all animals at sacrifice and evaluated by both rapid urease test and culture, as described above. In addition, to determine whether control animals developed a chronic infection and whether immunized animals were definitely *H. felis* negative, additional immunized and control animals were challenged as above but were not sacrificed until 4 weeks after challenge. The rate of protection among all immunized groups of animals was not appreciably different.

In order to not exclude possible low-level infection, scoring of the gastric biopsy specimens as positive or negative for *H. felis* growth was not done until 5 days after plating. From plating serial dilutions of known numbers (by hemacytometer count) of culture grown *H. felis*, it was observed that the sensitivity of this endpoint is approximately 10 organisms. In later experiments, biopsy culture plates were sometimes kept even longer than 5 days and when plates which remained negative for visible growth were scraped and examined by wet mount, an isolated spiral shaped organism could occasionally be seen. The identity of these isolated organisms could not be confirmed, and it could not be determined if they were viable. In any case, based on the culture results for serially diluted *H. felis*, it is believed that biopsy speciments which remained negative for visible growth at 5 days contained 10 or fewer bacteria.

Example 2

IgA and IgA monoclonal antibodies specific for *H. felis* were produced by a modification of the procedure of Mazanec et al[15] BALB/c mice obtained from the Jackson Laboratory (Bar Harbor, Maine) were immunized intragastrically four times over a 6-week period, the first three times with 2 mg of sonicated *H. felis* plus 10 μg of cholera toxin (Sigma Chemical Co., St. Louis, Mo.). For the last immunization, cholera toxin was omitted, and the mice also received an intravenous boost with 2 mg of *H. felis* protein. Three days later, the mice were sacrificed, and their spleen cells were hybridized to SP2/O myeloma cells. Clones, obtained by limiting dilution, were screened for secretion of anti-*H. felis* IgA antibody by an enzyme-linked immunosorbent assay (ELISA). The resulting cell line, identified as #71-$G_5$-$A_8$, was found to be a stable IgA secreting hybridoma. After multiple subclonings, stable IgA and IgG secretors were injected intraperitoneally into pristane-primed BALB/c mice, and the ascitic fluid was harvested and clarified.

The cell line #71-$G_5$-$A_8$, as of Apr. 13, 1992, is deposited in and maintained in viable condition in the Laboratory of Steven J. Czinn, M. D., Rainbow Babies and Children's Hospital, Room 465, Case Western University, 2074 Abington Road, Cleveland, Ohio, U.S.A. 44106. Access to the deposit will be available to a person determined by the U.S. Commissioner of Patents and Trademarks to be entitled thereto during pendency of the present application, and all restrictions on availability of the deposit to the public will be irrevocably removed upon grant of a patent on the application.

The cell line #71-$G_5$-$A_8$ is being deposited in the American Type Culture Collection, located at 12301 Parklawn Drive, Rockville, Md. 20852, U.S.A., under the identification number #71-$G_5$-$A_8$. The ATCC accession number and deposit date are, HB 11514 and Dec. 23, 1992, respectively.

Example 3

Passive immunization studies were carried out as follows. Ascites containing IgA monoclonal antibody produced from #71-$G_5$-$A_8$ (200μl) was administered intragastrically simultaneously with $10^6$ viable organisms. Preliminary studies indicated that gastric IgA titers of animals which received a single 200 μl dose of monoclonal IgA antibody declined to levels below that seen in actively immunized animals by 8 hours. Therefore, three additional doses of MAb were given over the next 24 hours. Control animals were challenged identically but received either saline or Sendai virus specific IgA monoclonal antibody (an irrelevant IgA monoclonal antibody). One week later, the mice were sacrificed. Gastric tissue was inoculated on Columbia blood agar plates and incubated for 5 days at 37° C. Infection was defined as a positive culture or a positive Stuart's rapid urease broth test.

To investigate whether IgA antibodies, the hallmark of the mucosal immune system, could by themselves protect against *H. felis* infection of the gastric mucosa, *H. felis* IgA monoclonal antibodies were generated as described above. One of these antibodies (#71-$G_5$-$A_8$) was then passively orally administered to germ-free mice at the time of and after challenge with *H. felis*. Control animals received either saline or Sendai virus specific IgA monoclonal antibody specific for the hemagglutinin-neuraminidase glycoprotein of Sendai virus[16].

The results are presented in Table 2.

TABLE 2

Evaluation of Passive Administration of Antibody To Germ-Free Mice Before and After Challenge with *H. felis*

| Antibody Administered | Number of of mice | Per Cent Infected |
|---|---|---|
| None-Control | 7 | 57% |
| Irrelevant IgA Monoclonal | 6 | 83% |
| IgA anti-*H. felis* monoclonal | 7 | 14% |

*H. felis* or Sendai virus specific IgA monoclonal antibody were given intragastrically 4 times over 24 hours concurrent with challenge with $10^6$ viable *H. felis*. Gastric biopsies were obtained 1 week after challenge and infection was determined by culture and/or rapid urease test.

Of the 13 control animals receiving no antibody or Sendai virus antibody, 70% were infected (FIG. 2B). Of the seven experimental animals, six were protected and only 1 (14%) was infected. By Chi Square analysis, the difference was significant (p=.019).

Comparison of antibody titers among experimental groups was evaluated by analysis of variance and Fisher's protected T test. For protection, absence or presence of experimental infection among groups were evaluated by Chi Square analysis.

REFERENCES

1. Blaser, M. J. "Gastric Campylobacter-like organisms, gastritis and peptic ulcer disease" Gastroenterology 1987, 93, 371–183.
2. Graham, D. Y. "Camplyobacter pylori and peptic ulcer disease" Gastroenterology 1989, 96, 615–625. .
3. Parsonnet, J., Vandersteen, D., Goates, J., Silbey, R. K., Pritkink, J. and Chang, Y. "Helicobacter pylori infection in intestinal and diffuse-type gastric adenocarcinomas" J. Natl. Cancer Inst. 1991, 93, 640–643.

4. Marshall B. J., Armstrong, J. A. and McGschie, D. B., "Attempt to fulfill Koch's postulate for pyloric Campylobacter" Med. J. Aust. 1985, 142, 436–439.

5. Morris, A. and Nicholson, H. "Ingestion of Campylobacter pyloridis causes gastritis and raised fasting gastric pH" Am. J. Gastroenterol. 1987, 82, 192–199.

6. Engstrand, L., Gustavsson, S., Jörgensen, A., Schwann, A., and Schaynius, A. "Inoculation of barrier-born pigs with Helicobacter pylori: a useful animal model for gastritis type B." Infect. Immun. 1990, 53, 1763–1768.

7. Fox, J. G., Cabot, E. B., Taylor, N. S. and Laraway, R. "Gastric colonization by campylobacter pylori subsp. mustelae in ferrets" Infect. Immun. 1988, 56, 2994–2996.

8. Fox, J. G., Pelayo, C., Taylor, N. S., Lee, A., Otto, G., Murphy, C. and Rose, R. "Helicobacter mustelae-associated gastritis in ferrets: an animal model of Helicobacter pylori gastritis in humans" Gastroenterology 1990, 99, 352–361.

9. Lee, A., Fox, J. G., Otto, G. and Murphy J. "A small animal model of human Helicobacter pylori active chronic gastritis" Gastroenterology 1990, 99, 1315–1323.

10. Fox, J. G., Lee, A., Otto, G., Taylor, N. S. and Murphy J. C. "Helicobacter felis gastritis in gnotobiotic rats: an animal model of helicobacter pylori gastritis" Infect. Immun. 1991, 59, 785–791.

11. Eaton, K. A., Morgan, D. R. and Krakowka, S. "Campylobacter pylori virulence factors in Gnotobiotic piglets" Infect. Immun. 1989, 57, 1119–1125.

12. Peterson, W. L. "Helicobacter pylori and peptic ulcer disease" N. Engl. J. Med. 1991, 324, 1043–1048.

13. Rauws, E. A. J., Langenberg, W., Houthoff, H. J., Zenon, H. C. and Tytgat, G. N. C. "Campylobacter pyloridis-associated chronic antral gastritis. A prospective study of its prevalence and the effects of antibacterial and antiulcer treatment" Gastroenterology 1988, 94, 33–40.

14. Fubara, E. S. and Freter, H. "Protection against enteric infection by secretory IgA antibodies" J. Immunol. 1973, 111, 395–403.

15. Offit, P. A. and Clark, H. F. "Protection against rotavirus-induced gastroenteritis in a murine model by passively acquired gastrointestinal but not circulating antibodies" J. Virol. 1985, 54, 58–64.

16. Mazanec, M. B., Nedrud, J. G. and Lamm, M. E. "Immunoglobulin A monoclonal antibodies protect against Sendai virus" J. Virol. 1987, 61, 2624–2626.

17. Winner, L. I., Mack, J., Weltzin, R., McKalanos, J. J., Kraehenbuhl, J. P. and Neutra, M. R., "New model for analysis of mucosal immunity: Intestinal secretion of specific monoclonal immunoglobulin A from hybridoma tumors protect against *Vibrio cholerae* infection" Infect. Immun. 1991, 59, 977–982.

18. Czinn, S. J. and Nedrud, J. G. "Oral Immunization against Helicobacter pylori" Infect. Immun. 1991, 59, 2359–2363.

19. Sawai, T., Hiruma, R., Kawana, N., Kaneko, M. Taniyasu, F. and Inami, A. "Outer membrane permeation of beta-lactam antibodies in *Eschericia coli*, Proteus mirabills and Enterobacter cloacae Antimicrob. Agents." Chemother, 1982, 22, 585–592.

20. Lowry, O. H., Rosebrough, N. J., Fart, A. J. and Randall, R. J. "Protein measurement with the folin phenol reagent" J. Biol. Chem. 1951, 193, 265–275.

21. Elson, C. O., Ealding, W. and Lefkowitz, J. "A lavage technique allowing repeated measurement of IgA antibody in mouse intestinal secretions" J. Immunol. Meth. 1984, 67, 101–108.

22. Nedrud, J. G., Liang, S., Hague, N. and Lamm, M. E. "Combined oral/nasal immunization protect mice from Sendai virus infection" J. Immunol. 1987, 139, 3484–3492.

23. Stuart, C., Van Stratum, E. and Rustigan, R. "Further studies on urease production by Proteus and related organisms" J. Bacteriol. 1945, 49, 437–444.

24. Czinn, S. J. and Cart, H. Rapid diagnosis of Campylobacter pyloridis-associated gastritis, J. Pediatr. 1987, 110–569–570.

25. Brandtzaeg, P. "Role of H chain and secretory component in receptor-mediated glandular and hepatic transport of immunoglobulins in man" Scan. J. Immunol. 1985, 22, 111–146.

26. Brandtzaeg, P., Bjerka, K., KEtt, K., Kvale, D., Rognum, T. O., Scott, H., Sollid, L. M. and Valnes, K. "Production and secretion of immunoglobulins in the gastrointestinal tract" Ann. Allergy 1987, 59, 21–39.

27. McDermott, M. R. and Bienenstock, J. "Evidence for a common mucosal immunologic system" I. migration of B. immunoblasts into intestinal, respiratory and genital tissues" J. Immunol. 1979, 122, 1892–1897.

28. Mestecky, J. "The common mucosal immune system and current strategies for induction of immune responses in external secretions" J. Clin. Immunol. 1987, 7, 265–276.

29. McGhee, J. R., Mestecky, J., Dertzbaugh, M. T., Eldridge, J. H., Hirasawa, M. and Kiyono, H. "The mucosal immune system from fundamental concepts to vaccine development" Vaccine 1992, 10, 75–88.

30. Holmgren, J., Clemens, J., Sack, D. A. and Svennerholm, A. M. "New cholera vaccines" Vaccines 1989, 7, 94–96.

31. Ogra, P. L., Karzon, D. T., Righthand, F. and Macgillivray, M. "Immunoglobulin response in serum and secretions after immunization with live and inactivated poliovaccine and natural infection" N. Engl. J. Med. 1968, 279, 895–900.

32. Wyatt, J. I., Rathbone, R. J. and Heatley, R. V. "Local immune response to gastritic campylobacter in non-ulcer dyspepsis" J. Clin. Path. 1986, 39, 863–870.

33. Kazi, J. I., Sinniah, R., Jaffrey, N. A., Alam S. M., Zaman, V., Zuberi, S. J. and Kazi, A. M. "Cellular and humoral immune response in campylobacter pylori-associated chronic gastritis" J. Pathol. 1989, 159, 231–237.

We claim:

1. A method of eliciting in a mammalian host a protective immune response to Helicobacter infection, comprising orally adminstering to the host an immunogenically effective amount of Helicobacter antigen with a mucosal adjuvant to elicit said protective immune response, wherein the Helicobacter antigen is a whole cell lysate preparation of at least one *Helicobacter felis* and *Helicobacter pylori*.

2. A method according to claim 1, wherein said mucosal adjuvant is cholera toxin.

3. A method according to claim 1, wherein said mammalian host is human.

4. A vaccine composition comprising an immunogenically effective amount of a whole cell lysate of Helicobacter antigen and a mucosal adjuvant in association with a pharmaceutically acceptable carrier or diluent, wherein the Helicobacter antigen is a whole cell lysate preparation of at least one of *Helicobacter felis* and *Helicobacter pylori*.

5. A Vaccine composition according to claim 4, wherein said mucosal adjuvant is cholera toxin.

\* \* \* \* \*